United States Patent [19]
Noda et al.

[11] Patent Number: 5,900,379
[45] Date of Patent: May 4, 1999

[54] ANALYTICAL DEVICE

[75] Inventors: Hiroto Noda, Kasuga, Japan; Benedict Zin, San Diego, Calif.

[73] Assignee: Mizuho USA, Inc., San Diego, Calif.

[21] Appl. No.: 08/631,795

[22] Filed: Apr. 11, 1996

[51] Int. Cl.[6] .............................................. G01N 33/533
[52] U.S. Cl. .......................... 436/518; 436/524; 436/530; 436/541; 436/807; 435/7.1; 435/7.93; 435/7.94; 435/287.7; 435/287.9; 435/288.7; 435/970; 422/56; 422/99; 422/58; 422/104; 422/59; 422/60
[58] Field of Search .................................. 422/56, 99, 58, 422/104, 59, 60; 435/7.1, 7.93, 7.94, 287.7, 287.9, 288.7, 970; 436/518, 524, 530, 541, 807

[56] References Cited

U.S. PATENT DOCUMENTS

| | | | |
|---|---|---|---|
| 2,350,239 | 5/1944 | Kohn | 40/158 |
| 2,770,572 | 11/1956 | Eldon | 167/84.5 |
| 3,074,853 | 1/1963 | Brewer | 167/84.5 |
| 3,232,710 | 2/1966 | Rieckmann | 23/253 |
| 3,502,437 | 3/1970 | Mass | 23/253 |
| 3,620,677 | 11/1971 | Morison | 23/253 |
| 3,666,421 | 5/1972 | Price | 23/253 |
| 3,672,845 | 6/1972 | Verbeck | 23/253 |
| 3,770,383 | 11/1973 | Price | 23/253 |
| 3,802,842 | 4/1974 | Lange et al. | 23/253 |
| 3,884,641 | 5/1975 | Kraffczyk et al. | |
| 3,990,850 | 11/1976 | Friedman et al. | 23/230 |
| 4,003,988 | 1/1977 | Hoff et al. | 424/12 |
| 4,272,381 | 6/1981 | Kremer et al. | 210/658 |
| 4,365,970 | 12/1982 | Lawrence et al. | 436/66 |
| 4,582,685 | 4/1986 | Guadagno et al. | 422/61 |
| 4,635,488 | 1/1987 | Kremer . | |
| 4,639,419 | 1/1987 | Olson et al. | 435/5 |
| 4,678,757 | 7/1987 | Rapkin et al. . | |
| 4,717,656 | 1/1988 | Swanljung | 435/7 |
| 4,742,002 | 5/1988 | Guadagno et al. | 435/28 |
| 4,789,629 | 12/1988 | Baker et al. | 435/7 |
| 4,857,453 | 8/1989 | Ullman et al. | 435/7 |
| 4,859,421 | 8/1989 | Apicella | 422/61 |
| 4,861,711 | 8/1989 | Friesen et al. | 436/70 |
| 4,877,580 | 10/1989 | Aronomitz et al. | 422/58 |
| 5,004,584 | 4/1991 | Rayman | 422/58 |
| 5,079,174 | 1/1992 | Buck et al. | 436/538 |
| 5,141,850 | 8/1992 | Cole et al. | 436/525 |
| 5,215,713 | 6/1993 | Steinbiss | 422/61 |
| 5,252,496 | 10/1993 | Kang et al. | 436/529 |
| 5,308,580 | 5/1994 | Clark | 422/58 |
| 5,356,782 | 10/1994 | Moorman et al. | 435/7.9 |
| 5,359,960 | 11/1994 | Yananton | 119/165 |
| 5,384,264 | 1/1995 | Chen et al. | 436/525 |
| 5,468,648 | 11/1995 | Chandler | 436/518 |
| 5,500,375 | 3/1996 | Lee-Own et al. | 436/514 |
| 5,504,013 | 4/1996 | Senior . | |
| 5,559,041 | 9/1996 | Kang et al. | 436/518 |
| 5,563,073 | 10/1996 | Titmas | 436/132 |
| 5,582,298 | 12/1996 | Clayton et al. | 206/569 |
| 5,589,398 | 12/1996 | Krause et al. | 436/164 |
| 5,602,040 | 2/1997 | May et al. | 436/514 |
| 5,607,863 | 3/1997 | Chandler | 436/518 |
| 5,611,433 | 3/1997 | Levy | 206/569 |
| 5,611,995 | 3/1997 | de Zoeten et al. | 422/58 |
| 5,622,871 | 4/1997 | May et al. | 436/514 |
| 5,648,274 | 7/1997 | Chandler | 436/514 |

FOREIGN PATENT DOCUMENTS

| | | | |
|---|---|---|---|
| 284 232 | 3/1988 | European Pat. Off. | G01N 33/558 |
| 291 194 | 4/1988 | European Pat. Off. | G01N 33/543 |
| 323 605 | 12/1988 | European Pat. Off. | G01N 33/558 |
| WO 88/08534 | 4/1988 | WIPO | G01N 33/543 |
| 94/01775 | 1/1994 | WIPO | G01N 33/544 |

*Primary Examiner*—James C. Housel
*Assistant Examiner*—Bao-Thuy L. Nguyen
*Attorney, Agent, or Firm*—Campbell & Flores LLP

[57] ABSTRACT

This invention relates to a novel analytical device for collecting, analyzing and storing of biological samples and, more specifically, to an analytical device used in the analysis of biological fluids such as urine.

19 Claims, 17 Drawing Sheets

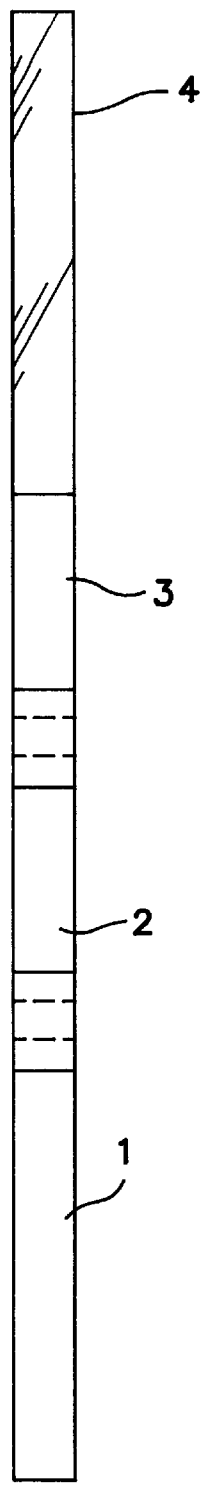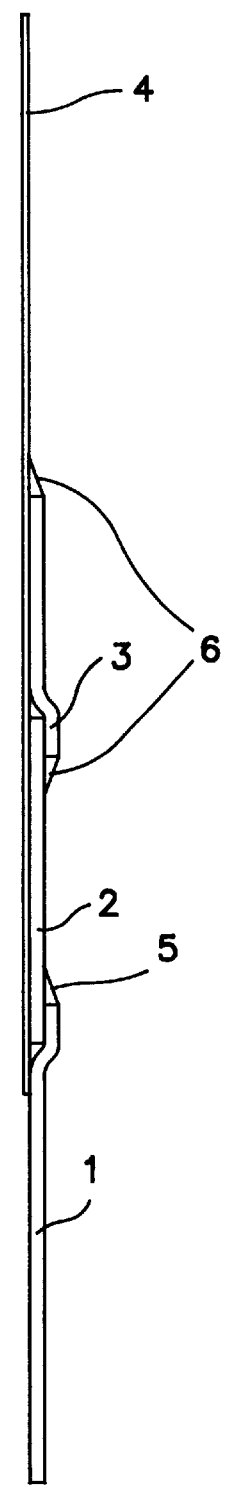
FIG. IA  FIG. IB

5,900,379

ANALYTICAL DEVICE

FIELD OF THE INVENTION

This invention relates to a novel analytical device for collecting, analyzing and storing biological samples, and, more specifically, to an analytical device used in the analysis of biological fluids such as urine.

BACKGROUND INFORMATION

The sampling and testing of biological fluids such as urine for the presence of analytes provides important information regarding various health related maters, including pregnancy and conception.

For an example, current test devices use an immunoassay for determining pregnancy or conception. At the heart of the immunoassay is a reagent, such as an antibody, that specifically reacts with an analyte to form a reaction complex. The immunoassay also can include and one or more separate detection reagents that react with the reaction product to facilitate detection of the reaction complex. The reaction complex can usually be detected by the unaided eye. An immunoassay can produce qualitative or semi-quantitative results.

Current pregnancy test devices assay for hormones associated with pregnancy, such as, for example, chorionic gonadotropin. Normally, the presence of human chorionic gonadotropin in urine is an indicator that a woman may be pregnant. Such test devices obtain qualitative results indicating either the presence or absence of chorionic gonadotropin. Typically, a pregnancy immunoassay contains an antibody directed against chorionic gonadotropin and a separate detection antibody.

Conception test devices also assay for hormones associated with the ovarian cycle, such as, for example, luteinizing hormone. Luteinizing hormone is present normally in urine but its concentration increases markedly during ovulation, the time at which a women is most likely to conceive. The probability that a woman can conceive a child thus increases with increasing concentration of luteinizing hormone. Such test devices obtain semi-quantitative results regarding the relative concentration of luteinizing hormone in the urine. Typically, a conception immunoassay contains an antibody directed against luteinizing hormone and a separate detection antibody.

Current test devices use various sample collection and analytical methods to detect an analyte in urine. For example, in one method urine is collected in a container and a measured urine volume transferred to a solution containing the immunoassay. The reaction product is detected in the resulting solution or as applied to a solid support. However, this method requires that the urine volume be accurately measured to insure the reaction product is not so diluted that it cannot be easily detected. In many situations, such as at-home testing, accurate measurement of urine volume is difficult perform and undesirable. Moreover, urine collection in a container and transfer to a test device generally is undesirable because of sanitary concerns and the potential for contamination.

In another method, the urine is collected in a container and transferred to a test device having an absorbent material that conducts or "wicks" the urine via capillary attraction to the immunoassay on a membrane. Typically, such a membrane immunoassay or absorbent material contains an antibody directed against the antigen of interest conjugated with a dye agent and an antibody directed to the antigen immobilized on the membrane immunoassay at a position "upstream" from the dye conjugate antibody. As the urine flows through the membrane immunoassay, the dye conjugate antibody binds the antigen and flows to the immobilized antibody where an antibody "sandwich" reaction complex is formed. A second absorbent material is positioned upstream from the immobilized antibody and in fluid flow contact with the membrane immunoassay to draw urine through the membrane immunoassay and collect urine and unbound dye conjugate antibody. The immobilized antibody typically is bound to the membrane in a line across the membrane immunoassay which results in a positive reaction appearing as a line.

A casing, usually made of plastic, surrounds the membrane immunoassay and the absorbent material in a manner that allows urine to be added only to the absorbent material. The absorbent material controls the volume of urine that contacts the immunoassay because only urine conducted by the absorbent material contacts the membrane immunoassay. Therefore, the volume of urine added to the absorbent material need not be accurately measured so long as a sufficient amount is added to allow the reaction to occur. An opening or window on one side of the casing over the membrane immunoassay permits the result to be observed. However, the collection of urine in a container and its transfer to the test device are disadvantages of the method because of sanitary concerns and the potential for contamination.

In another method, the urine is collected directly from the urine stream into the test device. The in-stream test device contains an absorbent material that is attached to and projects outward from a casing surrounding the above-described membrane immunoassay. The casing is designed as a handle to facilitate inserting the absorbent material into the stream during urination. The absorbent material is rigid so as to prevent being deflected out of the stream and not collecting a sufficient amount of urine. As described above, the absorbent material controls the amount of urine that contacts the membrane immunoassay and an opening or window on the casing permits the result to be observed. After collecting the urine, a cap may be placed over the absorbent material to contain the residual urine on the absorbent material and facilitate handling.

A disadvantage of current test devices is the relatively high cost to manufacture and use these test devices. A principle reason the test devices are expensive to manufacture is that each test device requires the manufacture and assembly of many separate parts. For example, an in-stream test device typically contains an absorbent material, a membrane immunoassay, a desiccant, two or more casing parts and a window. Each of these parts must be separately manufactured and then assembled in each test device which results in a high manufacturing cost for each test device.

Current test devices are expensive to use because each test device can only be used once. Since the cost of each test device is relatively high, a user incurs significant expense when multiple tests are required. For example, a conception test often requires testing for luteinizing hormone once a day for five or more days to optimize the probability of conception. The high cost of current test devices is a disadvantage particularly in underdeveloped regions of the world where the need for such test devices is great but cost significantly limits their use.

Another limitation of current test devices is that the result obtained cannot be conveniently stored. For example, urine soaked absorbent material contains microorganisms and the growth of such microorganisms in the absorbent material prohibits storage of the test device. Moreover, the result cannot be easily removed from the test device for separate storage from the absorbent material.

Yet another limitation of current test devices utilizing an absorbent material is that the result can only be observed from one side of the device. The ability to observe the result from more than one side would facilitate use, especially for in-stream test devices.

There thus is a need for a test device that detects analytes in urine which is more economical to manufacture and use than current test devices. There also is a need for a test device that allows the result to be archived for storage. Further, there is a need for a test device that allows the result to be viewed from more than one side of the device. Finally, the test device should be simple enough to used by the lay individual outside of a medical facility or any location such that medically trained individuals are not required to use the device. For instance, pregnancy tests are often conducted by the patient in her own home. The present invention satisfies these needs and provides related advantages as well.

SUMMARY OF THE INVENTION

This invention provides an analytical device for collecting and analyzing biological fluids, especially urine, which comprises a cassette containing an assay that can be easily inserted into and optionally removed from a casing.

The cassette is in the form of a strip having two ends and includes a first absorbent material, a membrane immunoassay, an optional second absorbent material and a cassette support means. The membrane immunoassay has a first end and a second end and comprises at least one reagent that forms a visible reaction complex indicating the presence of an analyte in fluid and a porous carrier capable of wicking aqueous fluid. The first absorbent material, the membrane immunoassay and the optional second absorbent material are arranged on and attached to the cassette support means such that the first absorbent material is at one end of the cassette and the first end of the membrane immunoassay is in fluid flow contact with the first absorbent material and the second end of the membrane immunoassay is in fluid flow contact with the second absorbent material.

The casing includes a fluid constriction opening, a channel extending from the fluid constriction opening into the casing that is the size of or larger than the cassette, one or more viewing areas, a sample collection opening, a stopping means and an optional supporting means. The sample collection opening is distal to the fluid constriction opening and the fluid constriction opening is a size that limits fluid flow to the membrane immunoassay to that through the first absorption material when the cassette is inserted into the channel to the stopping means. The viewing area is on the channel. The optional supporting means extends outward from the fluid constriction opening.

The cassette can be slidably inserted into the channel until stopped by the stopping means. The stopping means stops the cassette such that the first absorbent material extends beyond the fluid constriction opening and the membrane immunoassay is inside the casing and can be viewed through the viewing area.

In one embodiment, the casing further includes an aperture wherein the aperture is an opening to the channel at the opposite end of the casing from the fluid constriction opening and the cassette can be slidably inserted either through the fluid constriction opening or the aperture and into the channel until stopped by the stopping means. In a preferred embodiment of such a casing, the cassette is inserted through the aperture and the stopping means stops the cassette such that the cassette support means also extends beyond the aperture. In such an embodiment, the cassette optionally also can be removed from the casing through the aperture.

In another embodiment, the cassette support means is transparent and the viewing areas are on opposite sides of the casing.

In another embodiment, either the first absorbent material or the optional second absorbent material or both are detachably attached to the cassette support means. The analytical device further comprises a storage container having a closable open end that is the size of or larger than the cassette after removal of the first and second absorbent material.

In a preferred embodiment, the analytical device further comprises a cap. The cap has an open end and fits over the sample collection opening and, when present, the first absorbent material and optional support means to form a tight seal.

BRIEF DESCRIPTION OF THE DRAWINGS

FIGS. 1A and 1B are a top and side view of a cassette, respectively.

FIGS. 10B and 8C are front and side views of a storage means containing the cassette of FIG. 10A, respectively.

DETAILED DESCRIPTION OF THE INVENTION

Figure 2A:
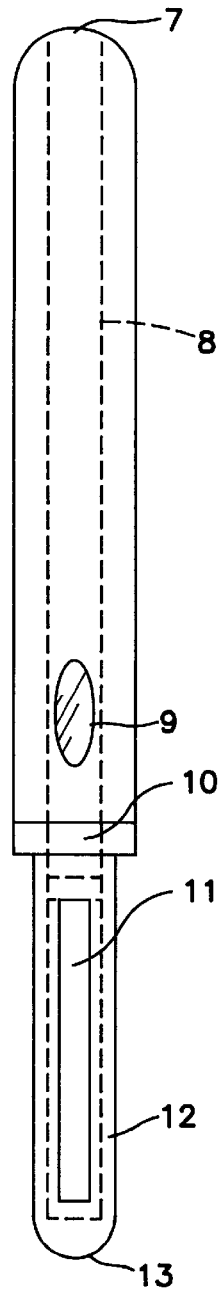
FIGS. 2A and 2D are front and side views of a casing, respectively.

The invention is an analytical device composed of a cassette and casing that are designed such that the cassette can be easily inserted into and, optionally, removed from the casing. The cassette contains analytical components for conducting an analysis and the casing facilitates handling the cassette during sample collection and analysis. The cassette is made in a strip format that is low-cost to produce and the casing is reusable. As a result, the analytical device can be manufactured and used at a lower cost than comparable current analytical devices.

The cassette is manufactured by attaching the analytical components on sheets to form a large sheet of bands. The cassettes are longitudinal strips cut from the large sheet of bands such that each cassette contains all the analytical components of the large sheet. This manufacturing method avoids the assembly of separate components in each analytical device and, thereby, significantly reduces the manufacturing costs.

A used cassette optionally can be removed from the casing and the casing reused by inserting another cassette. The reusable nature of the casing also results in reduced user costs, especially when many analyses by the same user are required.

After use, the cassette can be disposed of or the results section of the cassette can be stored. Storage is possible because the components of the cassette that otherwise prevent storage can be removed. For example, growth in the absorbent material of microorganisms present in the urine can be prevented because the absorbent material can be easily removed from the cassette. Thus, the result of the analysis can be stored without that portion of the analytical device containing most of the urine.

Another advantage of the invention is that the result can be observed through more than one viewing area. In one embodiment, the cassette contains the analytical components attached to a cassette support means that is a transparent material. The transparent material allows the result to be observed from either side of the cassette. Thus, an embodiment is a casing containing a viewing area on two sides, preferably opposite sides. Multiple viewing areas are advantageous, for example, because the device is easier to use since the user need not be conscious of which side of the device she views the result.

1. Definitions

The following definitions are used herein.

A "cassette" is a strip form containing a first absorption material, a membrane immunoassay and, optionally, a second absorption material arranged on a cassette support means. The first absorbent material and the second absorbent material are in capillary fluid flow contact with opposite ends of the membrane immunoassay. Capillary fluid flow contact can be achieved by any means including, for example, by end-to-end or overlap contact between the membrane immunoassay and the absorbent materials or via transport through a cassette support means made of a material capable of capillary attraction. The first absorbent material is at one end of the cassette so that fluid flows from the first absorbent material through the membrane immunoassay to the optional second absorbent material. Usually, the cassette contains all the analytical components needed to analyze for an analyte in the biological fluid.

A "first absorption material"0 is any bibulous, porous or fibrous material capable of rapidly absorbing an aqueous fluid and conducting the fluid via capillary attraction. Examples of such materials are those disclosed in H. J. Friesen, U.S. Pat. No. 4,861,711, issued Aug. 29, 1989, J. Bunting, U.S. Pat. No. 4,271,140, issued Jun. 2, 1981, European Patent Publication No. 0 284 232, European Patent Publication No. 0 291 194, and European Patent Publication No. 0 284 232. Preferred materials include paper, nitrocellulose, nylon, and silica gel.

The first absorbent material optionally can also comprise a mobile reagent that specifically binds to a analyte in the fluid to form a visible reactive complex with a reagent in the membrane immunoassay. Examples of such reagents are those disclosed in the above-discussed patents and applications. As discussed below, a preferred reagent is a mobile antibody directed against chorionic gonadotropin or luteinizing hormone conjugated to a colored latex sphere or colloidal metal.

The first absorbent material can be any size compatible with the casing so long as it is of a sufficient size to transport a sufficient amount of fluid to the membrane immunoassay in order to detect the analyte with the reagent(s) on the membrane immunoassay. The first absorbent material can be a single or multilayered absorbent material so long as the first absorbent material is in fluid flow contact with the membrane immunoassay.

A "membrane immunoassay" has a first and second end and comprises at least one reagent that forms a visible reaction complex indicating the presence of an analyte and a porous carrier capable of wicking aqueous fluid.

Any reagent known can be used in any known format such as, for example, sandwich and competitive binding formats, to specifically detect an analyte in a biological fluid such that a visible reaction complex is formed. Examples of such reagents are those disclosed in H. J. Friesen, U.S. Pat. No. 4,861,711, issued Aug. 29, 1989, J. Bunting, U.S Pat. No. 4,271,140, issued Jun. 2, 1981, European Patent Publication No. 0 284 232, European Patent Publication No. 0 291 194, and European Patent Publication No. 0 284 232. Such reagents can form a visible reaction complex with analytes such as, for example, hormones, proteins, haptens, immunoglobulin, polynucleotides, steroids, drugs, infectious disease agents (bacterial or viral) such as Streptoccus, Neisseria and Chlamydia.

Preferred reagents include antibodies to a hormone or infectious disease agent. Such antibodies include mobile antibodies conjugated to a signal agent or immobilized antibodies on the membrane. Mobile conjugated antibodies can be impregnated into the membrane immunoassay and, as discussed above, into the first absorbent material. The mobile conjugated antibodies are located downstream from a zone on the membrane immunoassay that contains immobilized antibodies. The mobile color conjugated antibodies bind to the hormone or infectious disease agent and are carried to the zone containing the immobilized antibodies where a sandwich antibody-hormone complex is formed and visualized. Preferred antibodies include anti-human chorionic gonadotropin antibodies and anti-human luteinizing hormone antibodies, especially murine monoclonal antibodies and especially those that have been affinity purified.

Preferred signal agents include colored latex spheres and colloidal metals. Such reagents and signal agents include those disclosed by D. Yost et al. U.S. Pat. No. 4,954,452, issued Sep. 4, 1990, J. Leuvering, U.S. Pat. No. 4,313,734, issued Feb. 2, 1982, P. Tarcha et al., U.S. Pat. No. 5,252,459, issued Oct. 12, 1993, T. Gribman et al., U.S. Pat. No. 4,373,932, issued Feb. 15, 1983 and R. Campbell, U.S. Pat. No. 4,703,013, issued Oct. 27, 1987.

The porous carrier of the membrane immunoassay is any bibulous, porous or fibrous material capable of rapidly absorbing an aqueous fluid and conducting the fluid via capillary attraction. Suitable materials are described, for example, in H. J. Friesen, U.S. Pat. No. 4,861,711, issued Aug. 29, 1989, J. Bunting, U.S. Pat. No. 4,271,140, issued Jun. 2, 1981, European Patent Publication No. 0 284 232, European Patent Publication No. 0 291 194, and European Patent Publication No. 0 284 232. Preferred porous materials include nitrocellulose, nylon, paper and silica gel. An advantage of a nitrocellulose membrane is that an immobilized antibody described above can be attached without prior chemical treatment. However, antibodies can be immobilized on other materials such as filter paper using well known chemical coupling methods such as, for example, CNBr, carbonyldimidazole or tresyl chloride.

The membrane immunoassay can be any size compatible with the casing that allows a reaction complex to be visualized.

The membrane immunoassay can be a single or multilayered membrane immunoassay so long as it forms a fluid flow contact with the first absorbent material and second absorbent material when present. For example, two or more membranes may be completely or partially layered over each other and each contain different reagents. In another example, a lower layer membrane can facilitate attachment of an upper layer membrane immunoassay to the cassette support means.

The membrane immunoassay also can be one continuous membrane immunoassay or several membrane immunoassays connected in series. For example, two membranes may be connected end-to-end and each contain different reagents.

An "optional second absorption material" is any bibulous, porous or fibrous material capable of rapidly absorbing an aqueous fluid and conducting the fluid via capillary attraction. Suitable materials are described, for example, in H. J. Friesen, U.S. Pat. No. 4,861,711, issued Aug. 29, 1989, J. Bunting, U.S. Pat. No. 4,271,140, issued Jun. 2, 1981, European Patent Publication No. 0 284 232, European Patent Publication No. 0 291 194, and European Patent Publication No. 0 284 232. Preferred materials include paper, nitrocellulose, nylon, and silica gel.

The second absorbent material can be any size compatible with the casing so long as it is of a sufficient size to aid capillary flow through the membrane immunoassay. The second absorbent material can be a single or multilayered so long as the second absorbent material forms a fluid contact with the membrane immunoassay.

A preferred second absorbent material also is a desiccant such as, for example, silica gel, that maintains the cassette in a dry state in a closed container.

A "cassette support means" is any material to which the first absorbent material, the membrane immunoassay and the optional second absorbent material can be attached to form a rigid, semi-rigid or flexible strip format. Preferred materials include, for example, plastics, particularly transparent plastic. Examples of suitable materials include polystyrene, polyproplyene and acrylic, polyvinyl chloride plastics.

A first absorbent material, membrane immunoassay and optional second absorbent material are "attached to" a cassette support means such that the components do not detach from the cassette prior to or during an analysis, fluid flow among the components is not prevented and the reaction in the membrane immunoassay is not inhibited. The first and second absorbent materials can be directly or indirectly attached to the cassette support means such as, for example, via the membrane immunoassay. Suitable attachment agents are well known in the art and include, for example, tape, glue and mechanical fasteners. Different attachment agents may be used for attaching the different components. A preferred attachment is to glue the membrane immunoassay to the cassette support means and tape the first absorbent material and the optional second absorbent material partially or completely to the membrane immunoassay. A preferred tape contains a moisture impermeable backing.

A "casing" is capable of receiving a cassette and contains a fluid constriction opening, viewing area, sample collection opening and an optional first absorbent material support means. A preferred casing also includes an aperture that opens the channel at the opposite side of the casing from the fluid constriction opening.

The casing is made of any moisture impermeable material including, for example, plastics such as polystyrene, polyproplyene, polyvinylchloride and acrylic. A preferred material is a transparent plastic, particularly polystyrene plastic.

The casing can be made by means known in the art appropriate for the material. For example, a casing made of plastic can be machined or molded, including injection and vacuum molded.

The casing can be made from one or more parts. If made from more than one part, the parts can be attached together by any known means appropriate for a material including snap fit, friction fit, welding, including laser welding, gluing and mechanical fastening.

Although a casing can be opaque, a preferred casing is transparent having a frosted exterior finish everywhere except at the viewing area. Polystyrene is a preferred plastic for making such a casing.

A "channel" is an opening in the casing the same size as or larger than the cassette such that the cassette can be inserted into or through the channel.

A "fluid constriction opening" is an opening to the channel. The fluid constriction opening limits fluid flow to the membrane immunoassay to that through the first absorbent material when the cassette is inserted fully into the casing. The fluid flow is limited by a friction fit between the fluid constriction opening and the first absorbent material. Optionally, the fluid constriction opening can include a flange extending into the channel to facilitate forming a friction fit with the first absorbent material.

A "viewing area" allows the result in membrane immunoassay to be seen. The viewing area includes, for example, an opening, an opening covered by a separate window part or a transparent casing. The viewing area can be on one or both sides of the membrane immunoassay.

An "optional supporting means" provides support for the first absorbent material such that the first absorbent material is not deflected by a fluid stream during sample collection, such as during in-steam urine collection. The supporting means is part of the casing extending outward from the fluid constriction opening and includes, for example, C channels which support the edges of the first absorbent material. An example of another supporting means includes a planar surface upon which the first absorbent material lies.

Alternatively, no supporting means is required if the sample collection does not involve a fluid stream. Further no supporting means is required if a sufficiently rigid cassette support means backs the first absorbent material.

An "aperture" is an opening at an end of the casing into which the cassette can be inserted or removed. Optionally, the aperture may be designed to facilitate the registration of the cassette in the casing by stopping the further insertion of the cassette into the casing.

The cassette can be inserted into the channel through either the fluid constriction opening or aperture so long as the cassette and casing are in proper registration to one another when the cassette is fully inserted. A "stopping means" provides such correct registration by insuring that the first absorbent material extends beyond the fluid constriction opening and the membrane immunoassay is inside the casing and visible in the viewing area when the cassette is fully inserted into the casing. In a casing containing an aperture, the stopping means preferably stops the cassette such that the cassette support means also extends beyond the aperture.

The stopping means can be located anywhere on the casing and/or cassette. In a casing containing only a fluid constriction opening, a preferred stopping means is the closed end of the channel. In a casing containing an aperture, preferred stopping means include a cross member to the support means, a flange on the cassette or a channel and cassette having symmetrical tapering sides.

A "storage container" has a closable open end that is the size of or larger than the cassette after removal of the first absorbent material and optional second absorbent material. A storage container is made of any moisture impermeable material including, for example, plastics such as polystyrene, polyproplyene and acrylic. A preferred material is a transparent plastic, particularly polystyrene plastic. The storage means optionally can contain reagents that inhibit the growth of microorganisms such as, for example, a chemical fixative or an antibiotic.

A "cap" has an open and closed ends and fits over the sample collection opening and, when present, the first absorbent material and optional support means to form a tight fit. The cap is made of any moisture impermeable material including, for example, plastics such as polystyrene, polyproplyene and acrylic. A preferred material is a transparent plastic, particularly polystyrene plastic. The cap forms a tight fit with the casing by any known means including, for example, a snap fit, friction fit, and mechanical fastening.

2. Examples of Embodiments of the Assay Device

FIG. 1 illustrates an embodiment of the cassette having a first absorbent material 1, a membrane immunoassay 2, an optional second absorbent material 3, and a cassette support means 4. The cassette has parallel sides and the first absorbent material 1, membrane immunoassay 2 and optional second absorbent material 3 are attached to cassette support means 4. The first absorbent material 1 and optional second absorbent material 3 are shown attached by tape 5 and 6, respectively. First absorbent material 1 is attached at one end of the cassette such that cassette support means 4 partially supports first absorbent material 1.

FIG. 2A illustrates a casing having an aperture 7, a channel 8, a viewing area 9, a fluid constriction opening 10, a sample collection opening 11, an optional supporting means 12 and a cross member 13. Channel 8 has parallel sides. Viewing area 9 is a transparent window. The optional supporting means includes cross member 13.

Figure 2B:
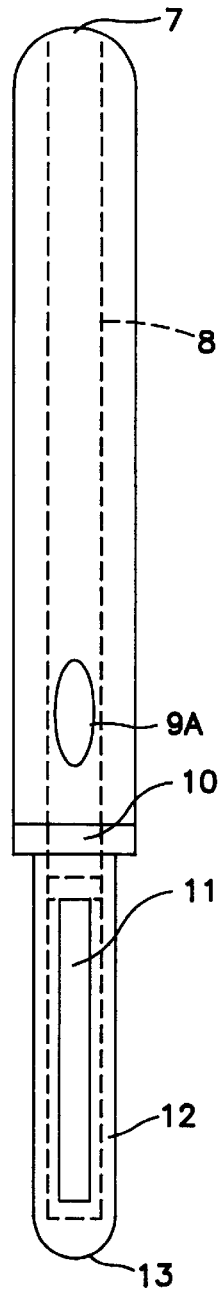
FIGS. 2B and 2E are front and side view of a casing, respectively.

FIG. 2B illustrates a casing containing a viewing area 9A that is an opening in the casing.

Figure 2C:
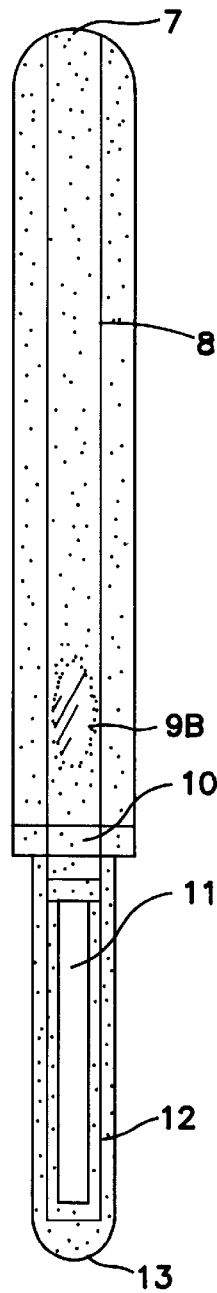
FIGS. 2C and 2F are front and side views of a casing, respectively.

FIG. 2C illustrates a casing made of transparent material having an exterior frosted finish everywhere except viewing area 9B.

Figure 2D:
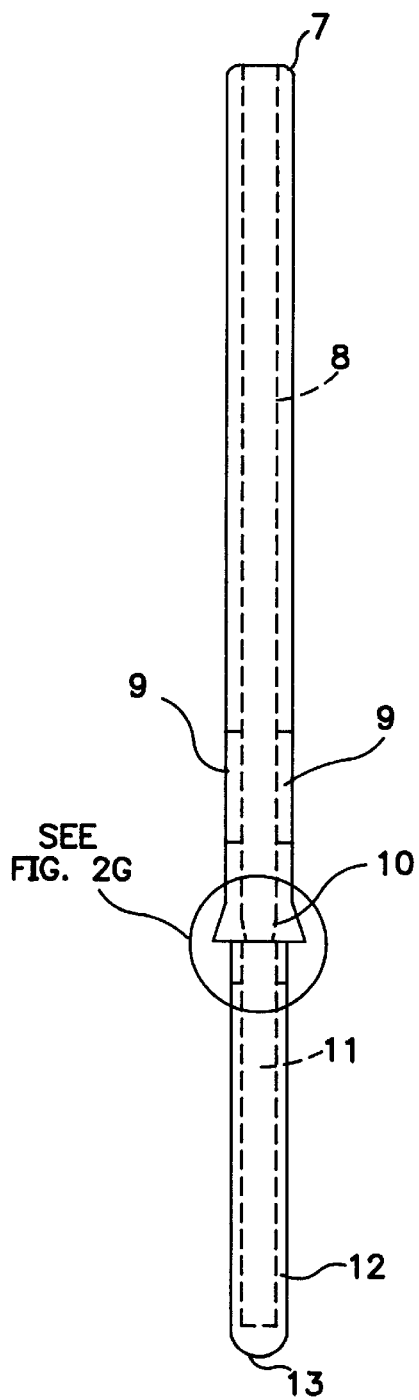

FIG. 2D illustrates a casing having a viewing area 9 on two sides of the casing.

Figure 2E:
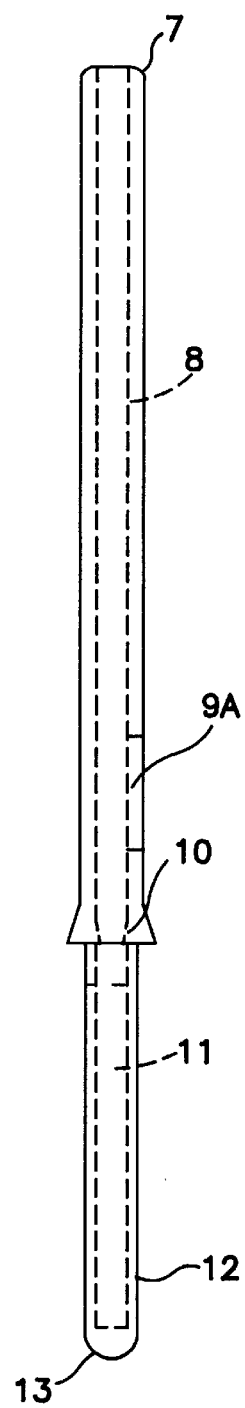

FIG. 2E illustrates a casing having a viewing area 9A on one side of the casing.

Figure 2F:
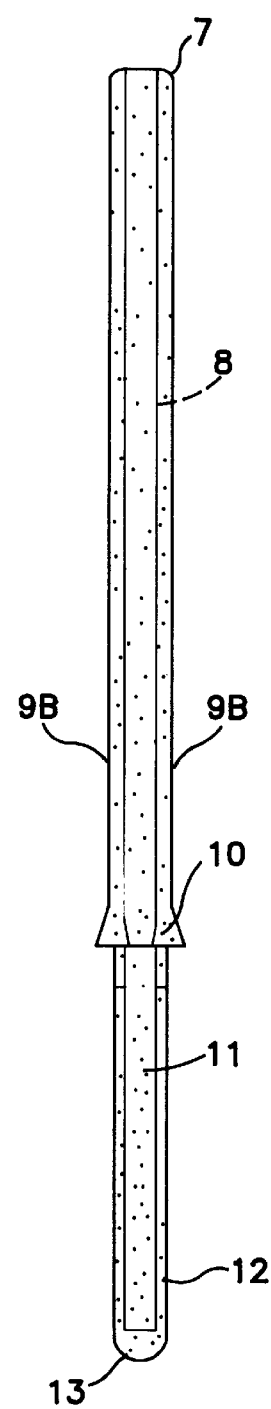

FIG. 2F illustrates a casing made of transparent material having an exterior frosted finish everywhere except the viewing area 9B on two sides of the casing.

Figures 2G, 2H:
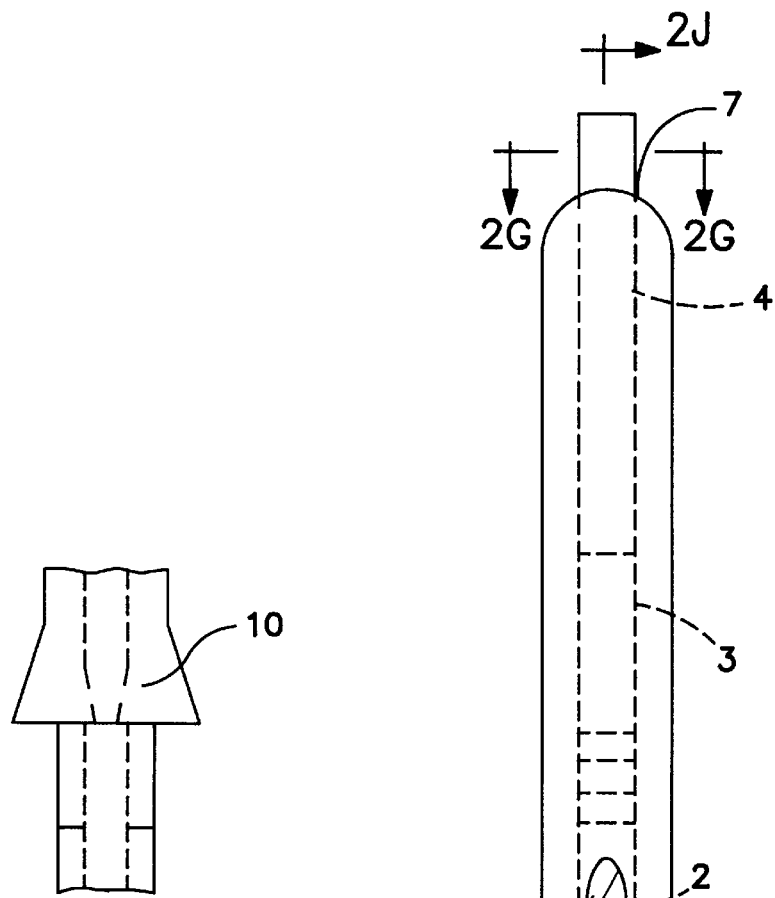
FIG. 2G is an exploded view of FIG. 2A.
FIG. 2H is a front assembled view of the cassette of FIG. 1 fully inserted into the casing of FIG. 2A and shows the section line of FIG. 2I and FIG. 2J.

FIG. 2G illustrates an exploded view of fluid constriction opening 10 in FIG. 2D showing a flange extending inwardly to the channel.

FIG. 2H illustrates the cassette of FIG. 1A fully inserted into the casing of FIG. 2A. The figure shows that first absorbent material 1 of the cassette extends beyond fluid constriction opening 10 of the casing. The figure shows membrane immunoassay 2 and optional absorbent material 3 are within the casing and membrane immunoassay 2 can be observed through viewing area 9. The figure also shows that cassette support means 4 extends beyond aperture 7 of the casing.

Figure 2I:
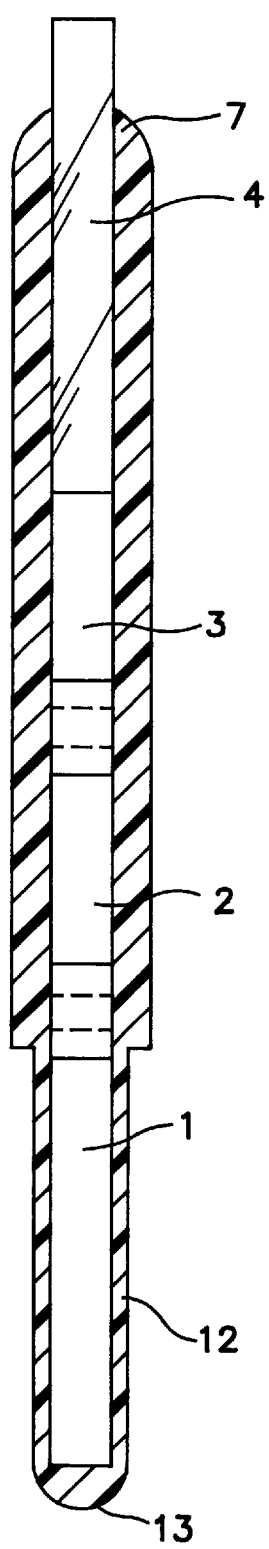
FIG. 2I is a cut-away view of the assembled cassette and casing of FIG. 2G.

FIG. 2I is an exploded view of FIG. 2H illustrating that cross member 13 of optional supporting means 12 stops the first absorbent material 1 of the cassette in the casing.

Figure 2J:
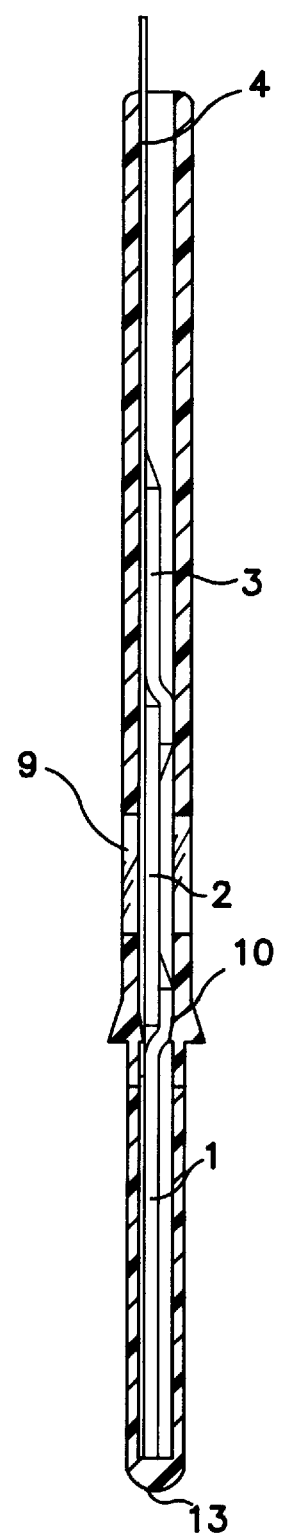
FIG. 2J is a cut-away view of the cassette of FIG. 1 fully inserted into the casing of FIG. 2G.

FIG. 2J illustrates an exploded view of FIG. 2H showing flange at fluid constriction opening 10 forming a friction seal with first absorption material 1 when the cassette is fully inserted into the casing. Such a friction seal restricts fluid flow to membrane immunoassay 2 to that through first absorption material 1.

Figure 3A:
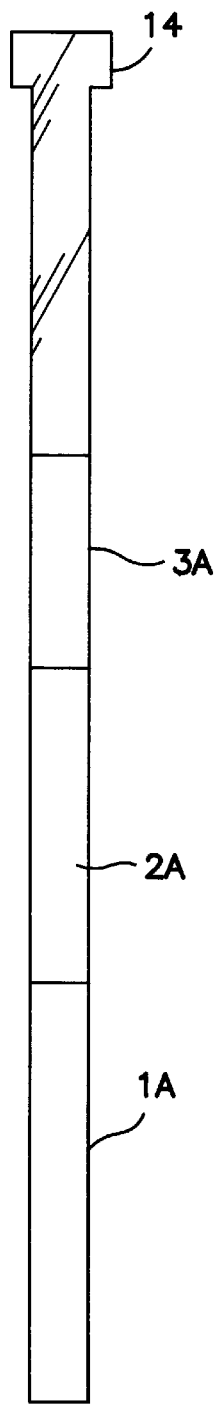
FIGS. 3A and 3B are front and side views of a cassette, respectively.

FIG. 3A illustrates a cassette having a flange on cassette support means 14 at the opposite end of the cassette from the first absorbent material.

Figure 3B:
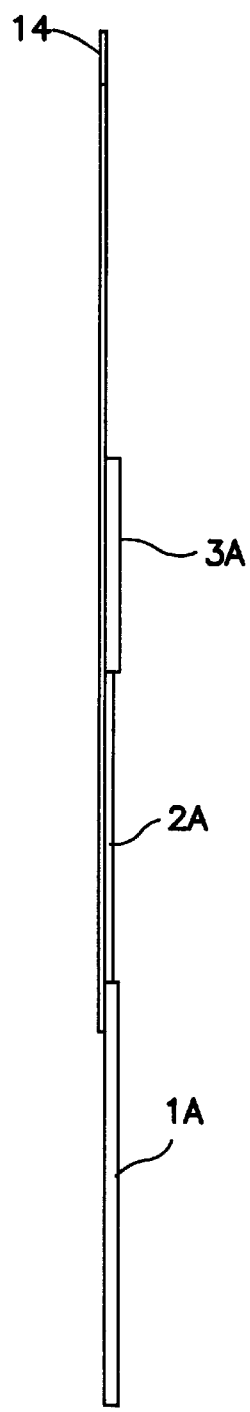
Figure 3C:
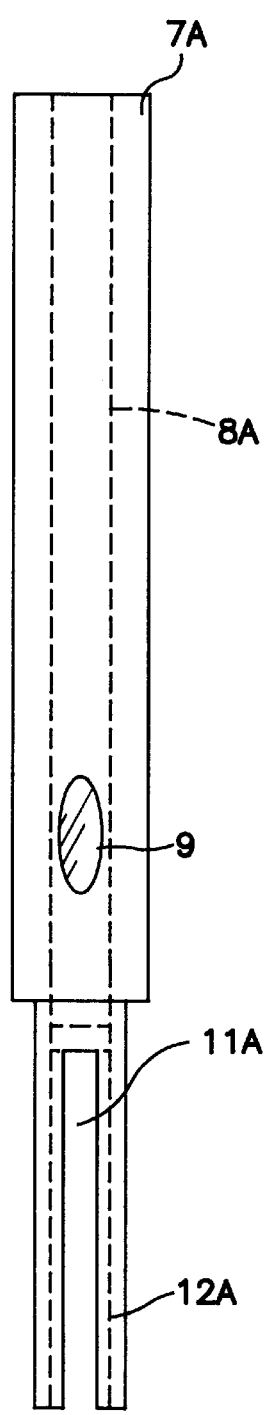
FIG. 3C is a front view of a casing.

FIG. 3C illustrates a casing having an optional supporting means 12A.

Figure 3D:
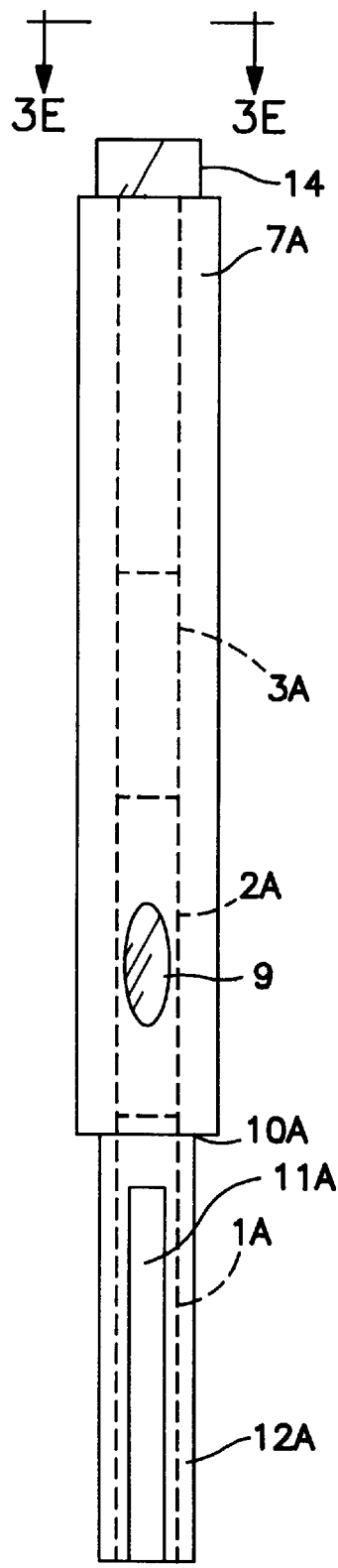
FIG. 3D is a front assembled view of the cassette in FIG. 3A fully inserted into the casing of FIG. 3C and shows the sectional line of FIG. 3E.
Figure 3E:
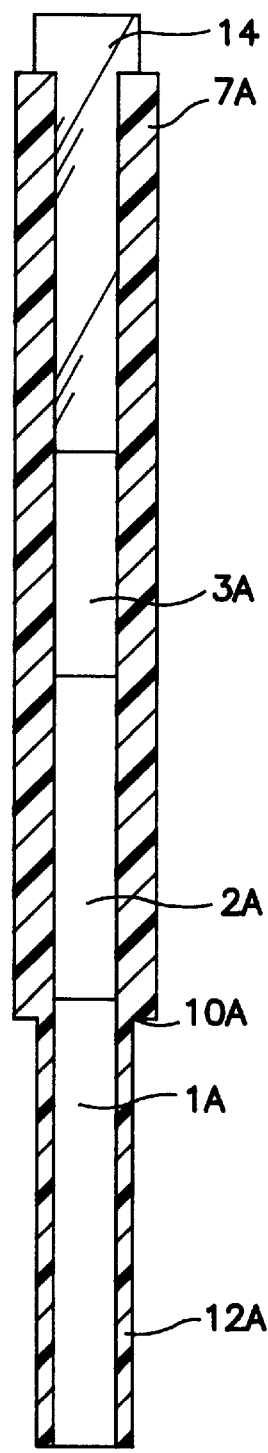
FIG. 3E is a cut-away view of the assembled cassette and casing of FIG. 3D.

FIGS. 3D and 3E illustrate the cassette of FIG. 3A fully inserted into the casing of FIG. 3B and that the flange of cassette support means 14 stops the cassette in the casing.

Figure 3F:
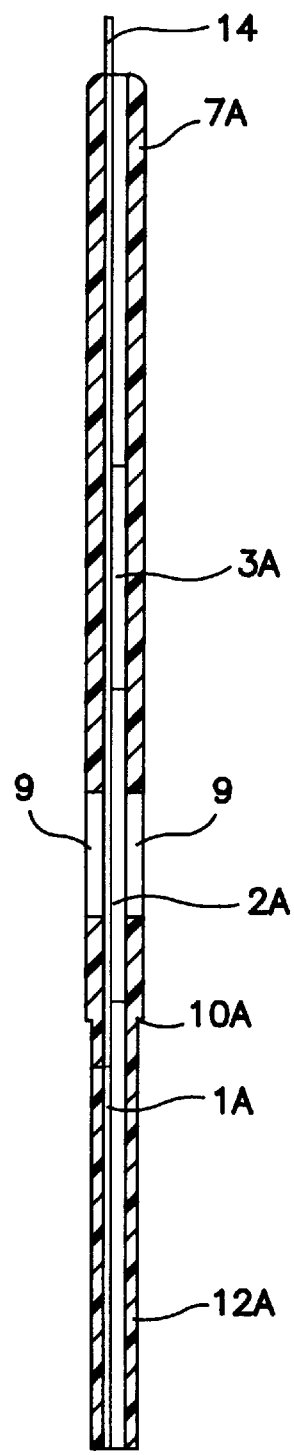
FIG. 3F is a cut-away view of the assembled cassette and casing of FIG. 3D.

FIG. 3F illustrates an exploded view of FIG. 3D showing fluid constriction opening 10 forming a friction seal with first absorption material 1 when the cassette is fully inserted into the casing.

Figure 4A:
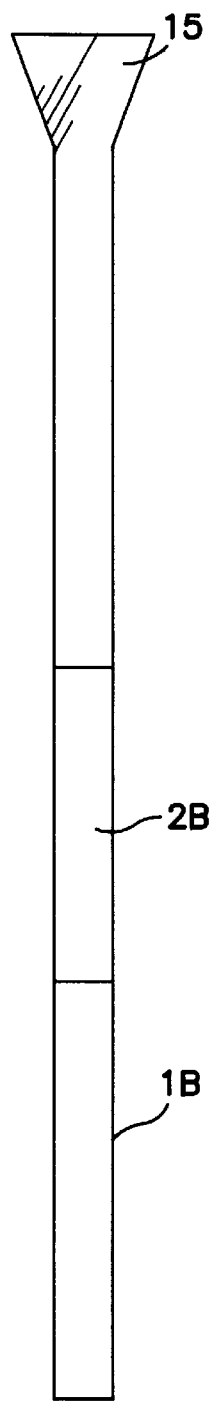
FIGS. 4A and 4B are front and side views of a cassette, respectively.
Figure 4B:
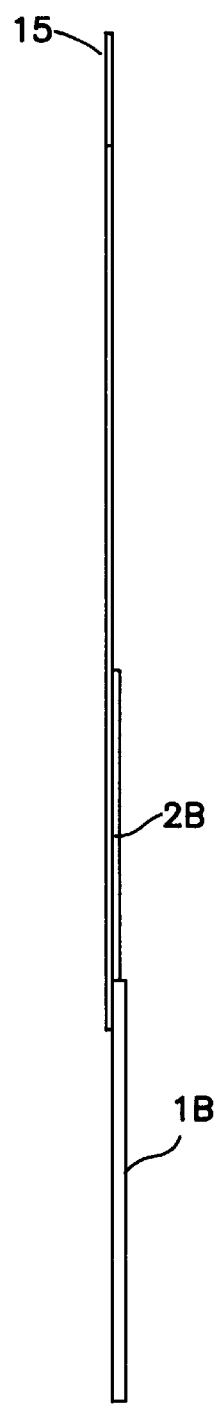

FIGS. 4A and 4B illustrate a cassette lacking the optional second absorbent material and having a flange on cassette support means 15 that is at the opposite end of the cassette from the first absorbent material.

Figure 4C:
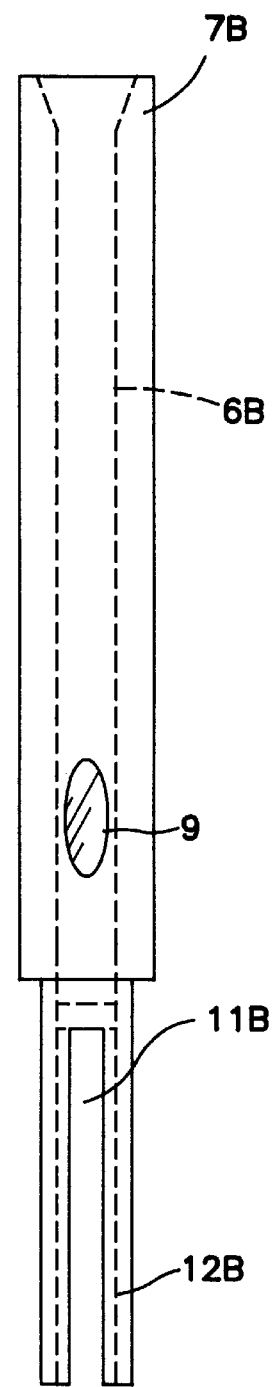
FIG. 4C is a front view of a casing.

FIG. 4C illustrates a casing having an aperture 7B in the form of a notch.

Figure 4D:
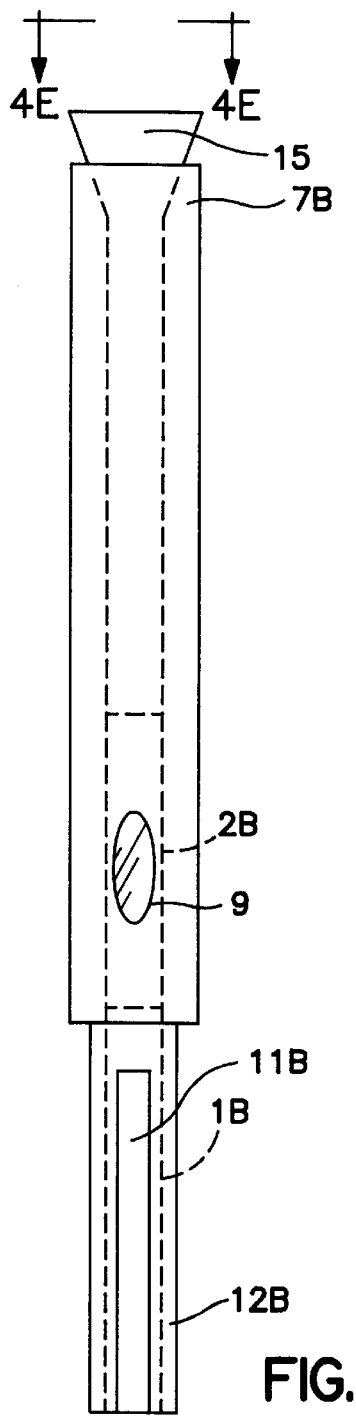
FIG. 4D is an front assembled view of the cassette of FIG. 4A fully inserted into the casing of FIG. 4C and shows the sectional line of FIG. 4E.
Figure 4E:
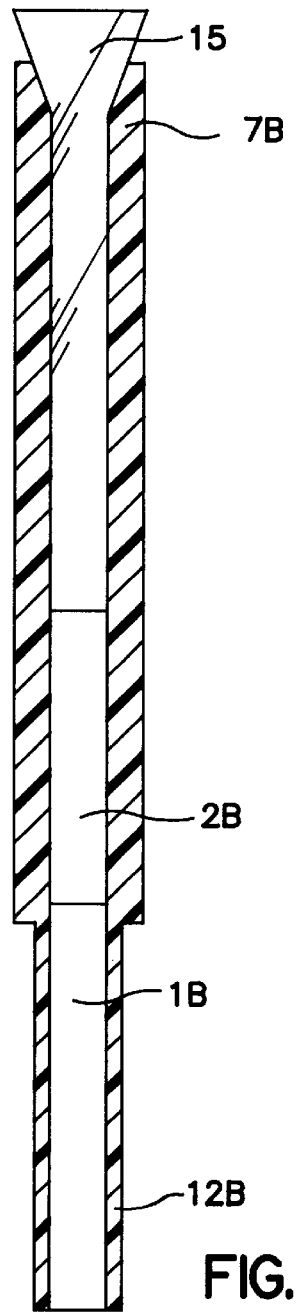
FIG. 4E is a cut-away view of the assembled cassette and casing of FIG. 4D.

FIGS. 4D and 4E illustrate the cassette of FIG. 4A fully inserted into the casing of FIG. 4C and that the flange of cassette support means 15 stops the cassette in the casing.

Figure 5A:
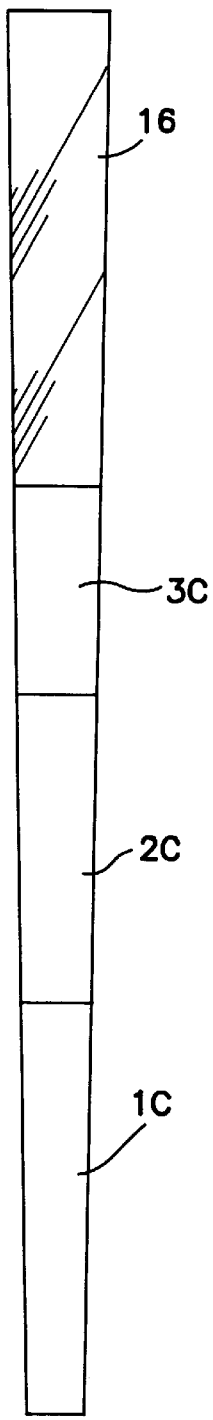
FIGS. 5A and 5B are front and side views of a cassette, respectively.

FIG. 5A illustrates a cassette having a tapered cassette support means 16.

Figure 5B:
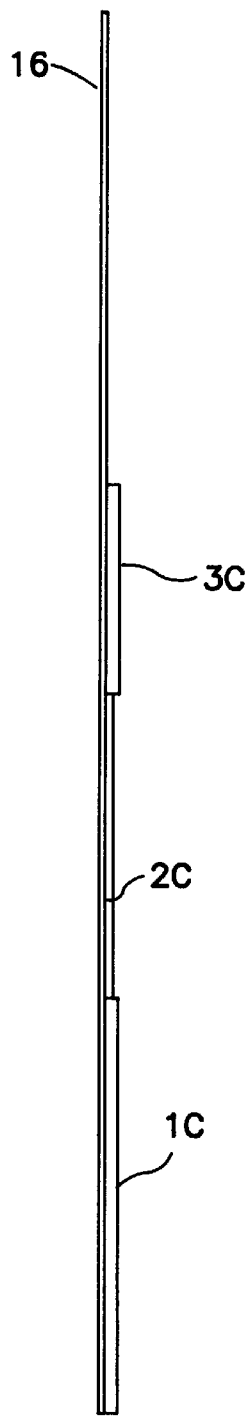

FIG. 5B illustrates a cassette in which cassette support means 16 fully supports first absorbent material 1.

Figure 5C:
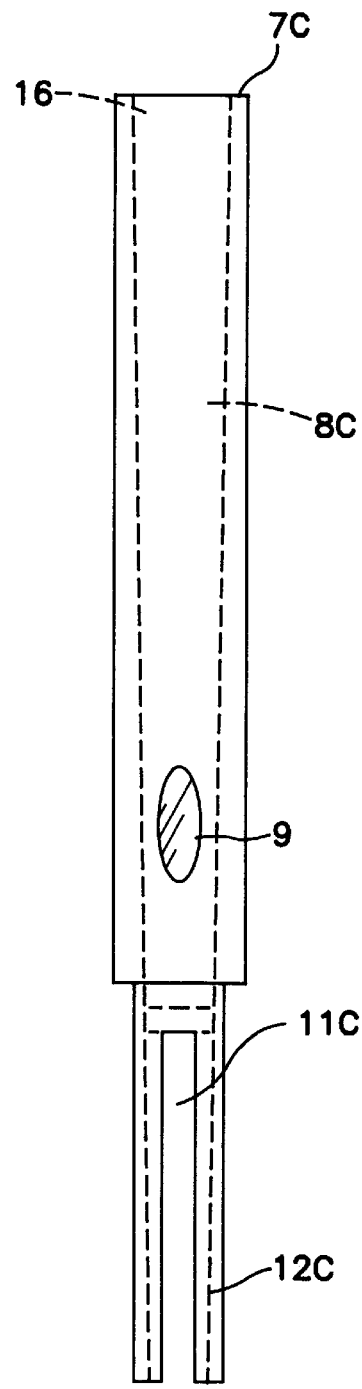
FIG. 5C is a front view of a casing.

FIG. 5C illustrates a casing having a channel 8C having tapered sides.

Figure 5D:
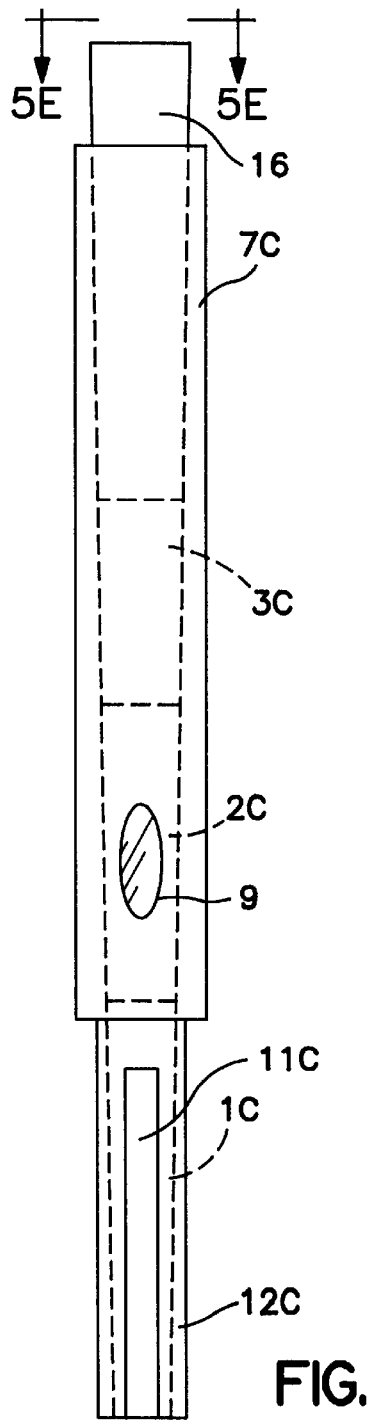
FIG. 5D is an a front assembled view of the cassette of FIG. 5A fully inserted into the casing of FIG. 5C and shows the sectional line of FIG. 5E.
Figure 5E:
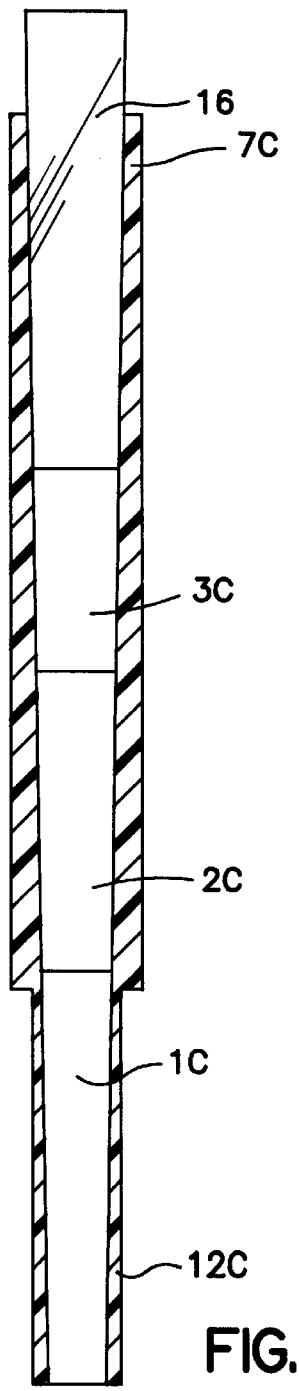
FIG. 5E is a cut-away view of the assembled cassette and casing of FIG. 5D.

FIGS. 5D and 5E illustrate the cassette of FIG. 5A fully inserted into the casing of FIG. 5C and that the tapered cassette support means 16 stops the cassette in the casing.

Figure 6A:
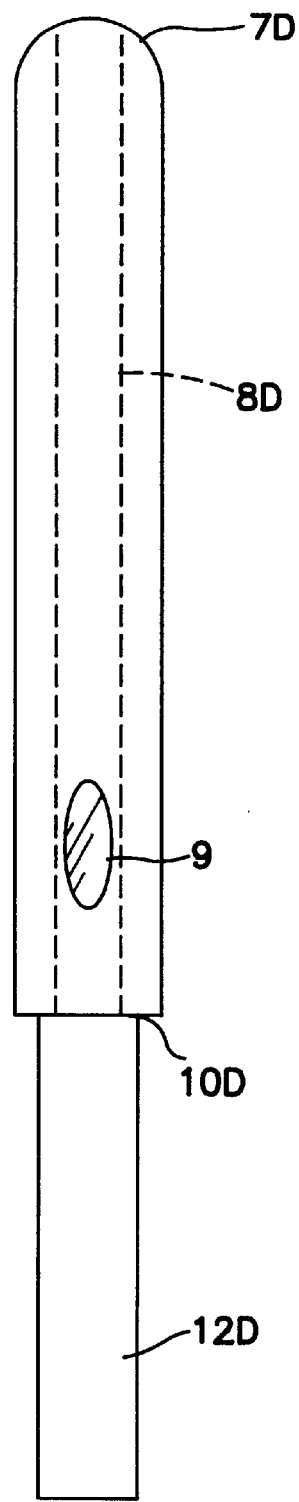
FIGS. 6A and 6B are front and side views of a casing, respectively.
Figure 6B:
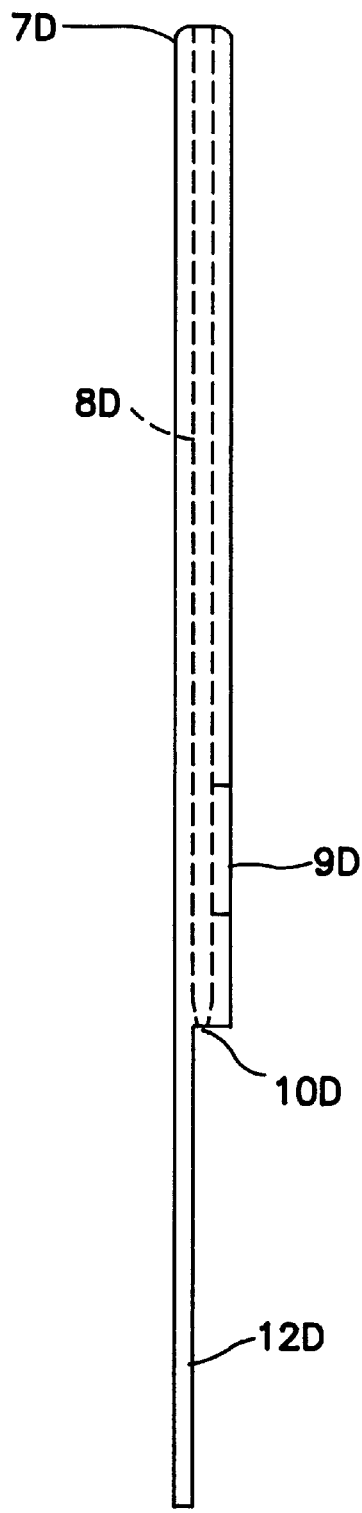

FIGS. 6A and 6B illustrate a casing having an optional support means 12D that is a planar structure extending outward from and below fluid constriction opening 10D.

Figure 6C:
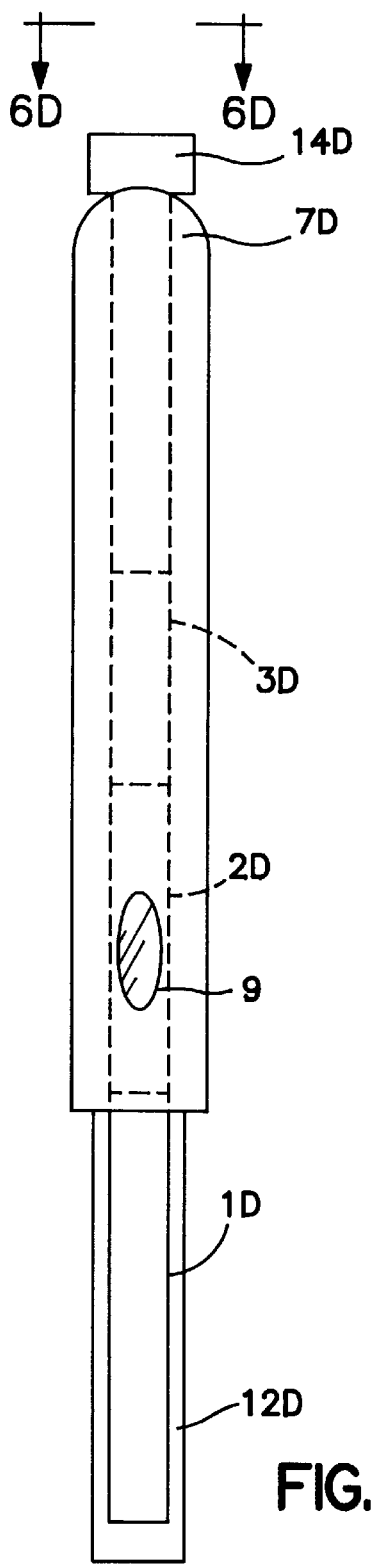
FIG. 6C is an a front assembled view of the cassette of FIG. 3A fully inserted into the casing of FIG. 6A and shows the sectional line of FIG. 6C.
Figure 6D:
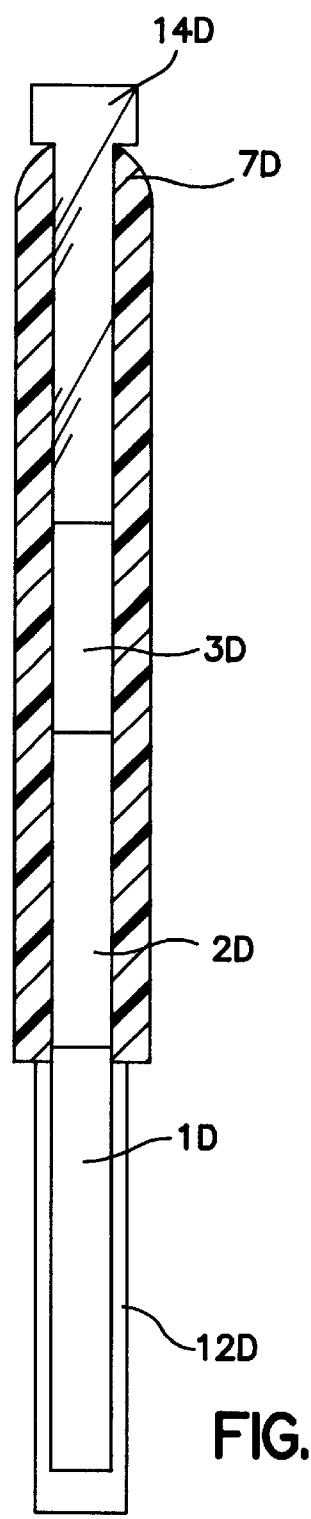
FIG. 6D is a cut-away view of the assembled cassette and casing of FIG. 6C.

FIGS. 6C and 6D show a cassette of FIG. 3A fully inserted into the casing of FIG. 6A and cassette support means 14D stops the insertion of the cassette.

Figure 7A:
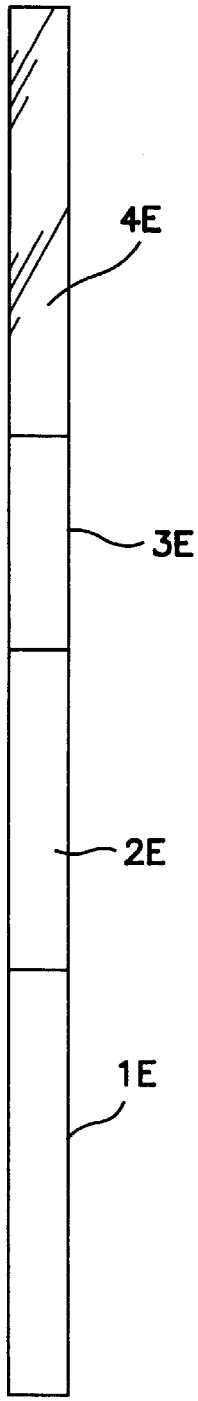
FIGS. 7A and 7B are a front views of a cassette and casing, respectively.
Figure 7B:
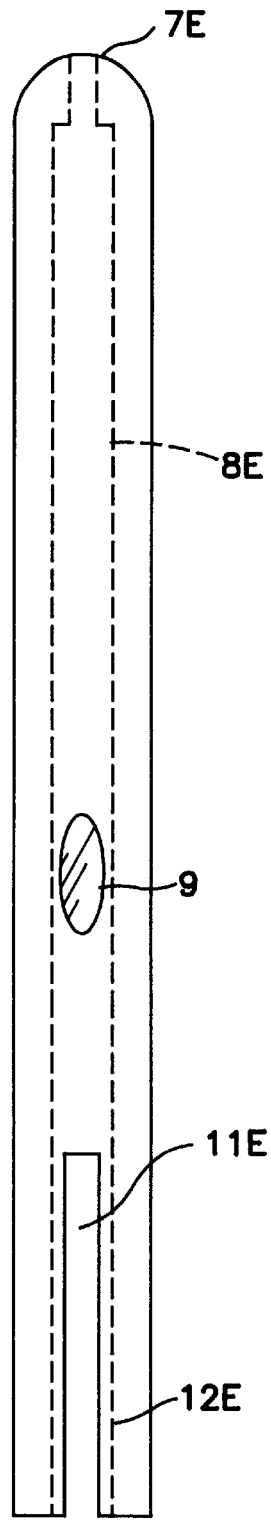

FIG. 7B illustrates a cassette into which the cassette of FIG. 7A is inserted through constriction aperture opening 10E.

Figure 7C:
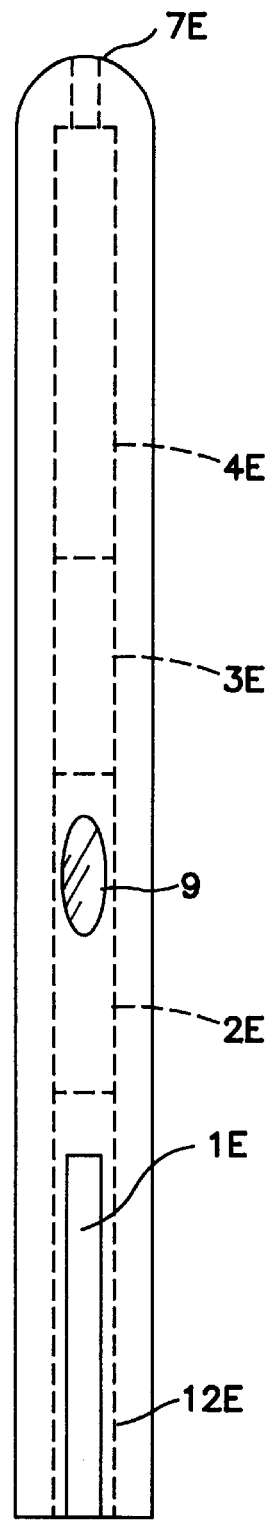
FIG. 7C is a front assembled view of the cassette of FIG. 7A fully inserted into the casing of FIG. 7B.

FIG. 7C illustrates the cassette of FIG. 7A fully inserted into the casing of FIG. 7B and that aperture 7F stops the cassette in the casing.

Figure 8A:
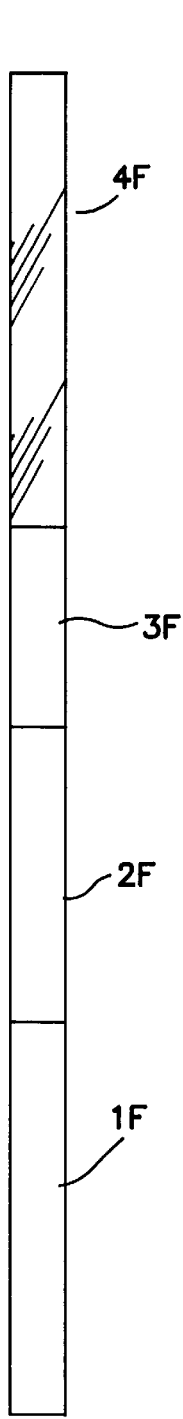
FIGS. 8A and 8B are front and side views of a cassette, respectively.
Figure 8B:
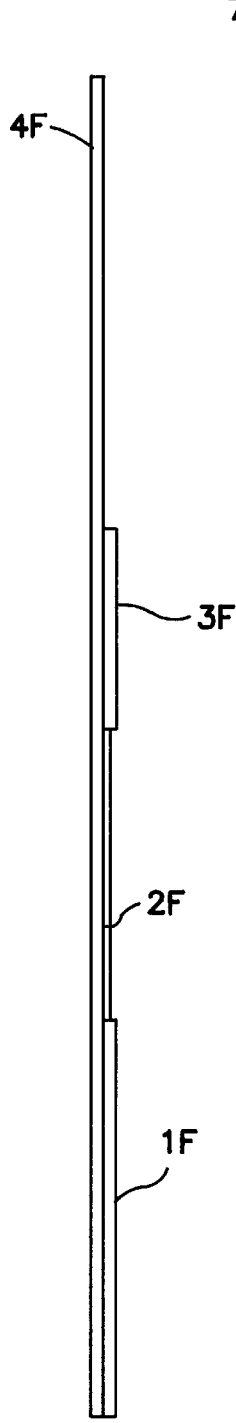

FIGS. 8A and 8B illustrate a cassette having a cassette support means 4F sufficiently rigid to support first absorbent material 1 in a urine stream.

Figure 8C:
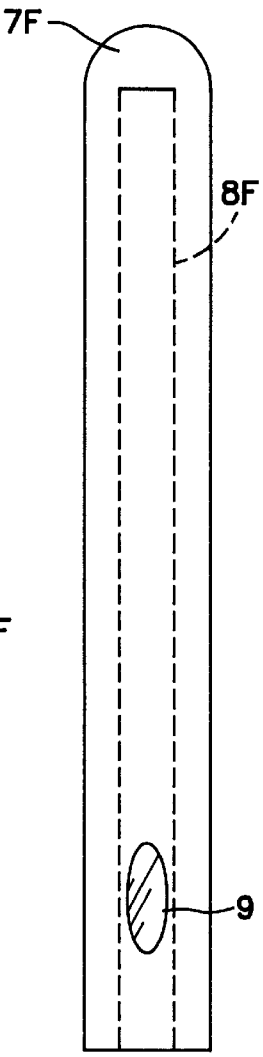
FIG. 8C is a front view of a casing and FIG. 8D is a front assembled view of the cassette of FIG. 8A fully inserted into the casing of FIG. 8C.

FIG. 8C illustrates a cassette only having a fluid constriction opening 10F to channel 8F and lacking an optional supporting means.

Figure 8D:
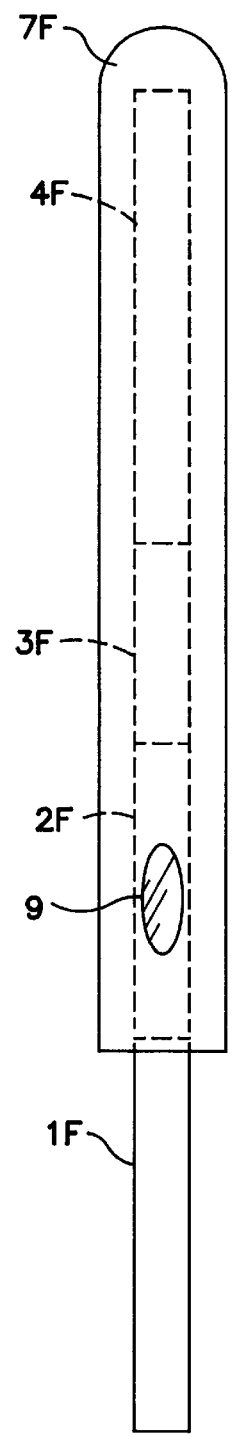

FIG. 8D illustrates the cassette of FIG. 8A fully inserted into the casing of FIG. 8C and the casing stops the cassette.

Figure 9A:
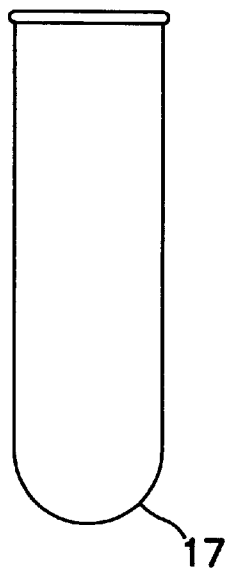
FIGS. 9A and 9B are front and side views of a cap, respectively.
Figure 9B:
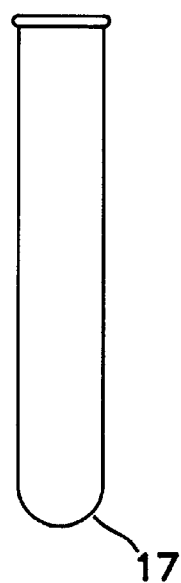
Figure 9C:
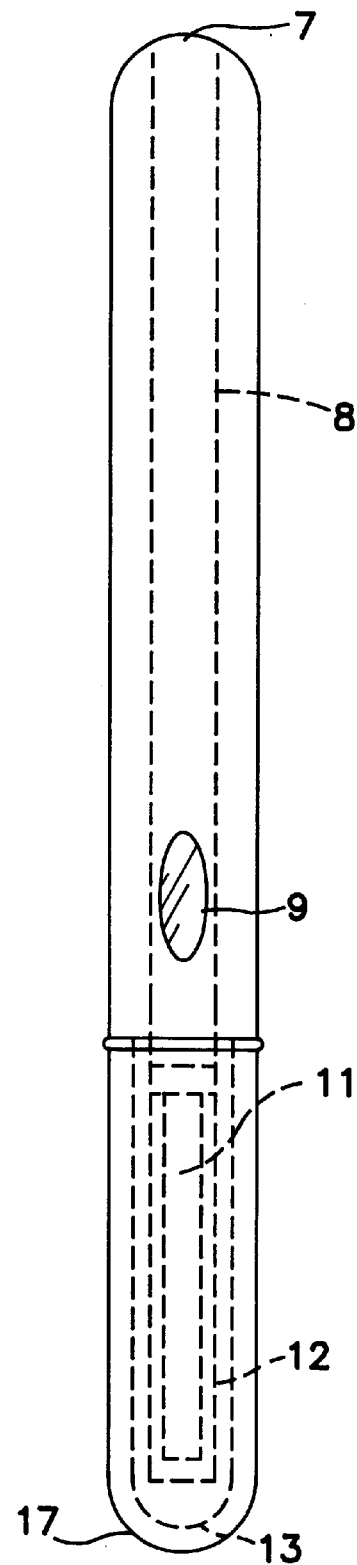
FIG. 9C is an assembled view of the cap on the casing of FIG. 2A.

FIGS. 9A and 9B illustrate a cap 17. FIG. 9C illustrates cap 17 attached to the casing of FIG. 2A.

Figure 10A:
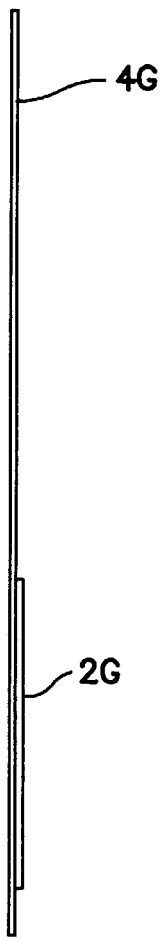
FIG. 10A is a side view of the cassette of FIG. 1 after the first absorbent material and optional second absorbent material have been removed.

FIG. 10A illustrates the cassette of FIG. 1 from which the first and optional second absorbent materials have been removed.

Figure 10B:
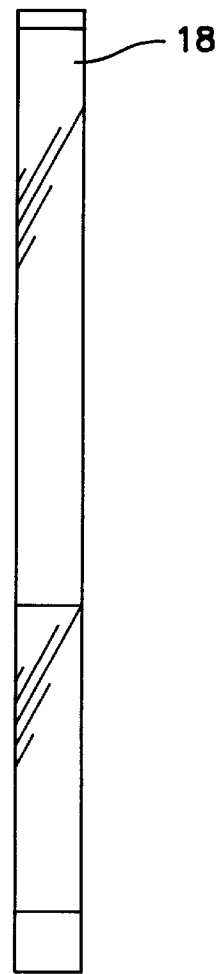
Figure 10C:

FIGS. 10B and 10C illustrate a storage means 18 containing the cassette of FIG. 10A.

EXAMPLE I

Specimen Collection and Analysis

The following example illustrates collecting an in-stream urine sample and detecting the presence of chorionic gonadotropin suing the analytical device illustrated in FIGS. 1 and 2A.

A cassette containing an membrane immunoassay to detect human chorionic gonadotropin, is selected.

The cassette is inserted with the first absorbent material end first into the aperture until stopped by the cross member of the optional supporting means.

The assembled analytical device is inspected to determine if the cassette and casing are in correct registration by observing, for example, that the first absorbent material extends beyond the fluid constriction opening, the cassette support means extends beyond the aperture and the membrane immunoassay can be seen through the viewing area. FIG. 2H show the cassette inserted into the casing in correct registration.

Conventional in-stream urine collection procedures are then used to collect a sample. A sample can be collected at any time of day, but for best results, it is best to test the first urine of the morning because it contains the highest concentration of chorionic gonadotropin. After urination has started, the first absorbent material of the analytical device is inserted into the urine stream until the entire first absorbent material is wet, about five seconds. If the analytical device has a viewing area that is open, care should be taken to avoid urine from entering through the viewing area.

The analytical device is removed from the urine stream with the first absorbent material end pointing downwards. Optionally, the cap may be placed over the first absorbent material.

The result is obtained usually in about two to five minutes and appears in the viewing area. Any indication of a positive reaction indicates pregnancy.

After the analysis, the cassette can be removed from the casing, casing washed and reserved for a subsequent analysis. The cassette can be discarded or the first and optional second absorbent material can be removed and the result stored in the storage means.

All publications patents and patent applications cited herein are expressly incorporated by reference.

Many other objects, features, and advantages of the present invention will be apparent to those of skill in the art.

Although the invention has been described with reference to the figures and Examples provided above, it should be understood that various modifications can be made by those skilled in the art without departing from the invention. Accordingly, the invention is set out in the following claims.

We claim:

1. An analytical device comprising:
   a) a cassette in the form of a strip having two ends and including:
      a first absorbent material;
      an immunoassay membrane having a first end and a second end comprising at least one immobilized reagent that forms a visible reaction complex indicating the presence of an analyte in fluid and a porous carrier that wicks aqueous fluid;
      an optional second absorbent material; and
      a cassette support means, wherein:
         the first absorbent material, the immunoassay membrane and the optional second absorbent material are arranged on and attached to the cassette support means such that the first absorbent material is at one end of the cassette; and
         the first end of the immunoassay membrane is in fluid flow contact with the first absorbent material and the second end of the membrane immunoassay is in fluid flow contact with the optional second absorbent material; and
   b) a casing including:
      a fluid constriction opening;
      a channel extending from the fluid constriction into the casing that is the size of or larger than the cassette;
      an aperture;
      one or more viewing areas;
      a sample collection opening;
      a stopping means; and
      an optional supporting means, wherein:
         the fluid constriction opening is a size that limits fluid flow to the immunoassay membrane such that fluid flows through the first absorption material when the cassette is inserted into the channel to the stopping means;
         the viewing area is on the channel;
         the sample collection opening is distal to the fluid constriction opening;
         the optional supporting means extends outward from the fluid constriction opening;
         the cassette is slidably inserted through the fluid constriction opening and into the channel until stopped by the stopping means;
         the stopping means stops the cassette such that the first absorbent material extends beyond the fluid constriction opening and the immunoassay membrane is inside the casing and the visible reaction complex is visible in the viewing area.

2. An analytical device comprising:
   a) a cassette in the form of a strip having two ends and including:
      a first absorbent material;
      an immunoassay membrane having a first end and a second end comprising at least one immobilized reagent that forms a visible reaction complex indicating the presence of an analyte in fluid and a porous carrier that wicks aqueous fluid;
      an optional second absorbent material; and
      a cassette support means, wherein:
         the first absorbent material, the immunoassay membrane and the optional second absorbent material are arranged on and attached to the cassette support means such that the first absorbent material is at one end of the cassette; and the first end of the immunoassay membrane is in fluid flow contact with the first absorbent material and the second end of the immunoassay membrane is in fluid flow contact with the optional second absorbent material; and b) a casing including:
   a fluid constriction opening;
   a channel extending from the fluid constriction into the casing that is the size of or larger than the cassette;
   an aperture;
   one or more viewing areas;
   a sample collection opening;
   a stopping means; and
   an optional supporting means, wherein:
      the fluid constriction opening is a size that limits fluid flow to the immunoassay membrane such that fluid flows through the first absorption material when the cassette is inserted into the channel to the stopping means;
      the aperture is an opening to the channel at the opposite end of the casing from the fluid constriction opening;
      the viewing area is on the channel;
      the sample collection opening is distal to the fluid constriction opening;
      the optional supporting means extends outward from the fluid constriction opening;
      the cassette is slidably inserted either through the fluid constriction opening or the aperture and into the channel until stopped by the stopping means;
      the stopping means stops the cassette such that the first absorbent material extends beyond the fluid constriction opening and the immunoassay membrane is inside the casing and the visible reaction complex is visible in the viewing area.

3. The analytical device according to claim 2, wherein the cassette is slidably inserted through the aperture and into the channel until stopped by the stopping means.

4. The analytical device according to claim 3, wherein the stopping means stops the cassette such that the cassette support means also extends beyond the aperture.

5. The analytical device according to claim 4, wherein the cassette is removed from the casing through the aperture.

6. The analytical device according to claim 3, wherein the optional supporting means is present and contains a cross member that contacts the first absorption material and stops the insertion of the cassette into the casing.

7. The analytical device of claim 6, wherein the optional supporting means is present and forms more than one sample collection opening.

8. The analytical device according to claim 3, wherein the cassette support means has a flange at the end opposite the first absorbent material that is larger than the aperture and stops the insertion of the cassette into the casing.

9. The analytical device according to claim 3, wherein the aperture is a notch and the cassette support means has a flange at the opposite end from the first absorbent material that stop the insertion of the cassette into the casing.

10. The analytical device according to claim 3, wherein the channel forms a taper that is wider at the aperture than at the fluid constriction opening and the cassette forms a taper that is wider at the opposite end from the first absorbent material than at the first absorbent material end that stop the insertion of the cassette into the casing.

11. The analytical device of claim 1 or claim 2, wherein the cassette support means is transparent.

12. The analytical device of claim 11, wherein two viewing areas are on opposite sides of the casing.

13. The analytical device of claim 1 or claim 2, wherein the optional supporting means is two C channels extending outward from the fluid constriction opening on opposite sides of the casing opening inward and into which the first absorbent can slidably move.

14. The analytical device of claim 1 or claim 2, wherein the optional supporting means is a planar surface extending outward from one fluid constriction opening.

15. The analytical device of claim 1 or claim 2, wherein either the first absorbent material or the optional second absorbent material or both are detachably attached to the cassette support means.

16. The analytical device of claim 15, further comprising a storage container having a closable open end that is the size of or larger than the cassette after removal of the first absorbent material and optional second absorbent material.

17. The analytical device of claim 1 or claim 2, further comprising a cap having an open and closed end that fits over the sample collection opening and, when present, the first absorbent material and optional support means to form a tight fit.

18. The analytical device of claim 1, wherein the immobilized reagent that forms the visible reaction in the immunoassay membrane is an immobilized antibody.

19. The analytical device of claim 2, wherein the immobilized reagent that forms the visible reaction in the immunoassay membrane is an immobilized antibody.

* * * * *